United States Patent [19]

Arnold et al.

[11] Patent Number: 4,735,692

[45] Date of Patent: Apr. 5, 1988

[54] PHOSPHATE SELECTIVE MEMBRANE ELECTRODE AND METHOD OF DETERMINING PHOSPHATE

[75] Inventors: Mark A. Arnold, Coralville; Scott A. Glazier, Iowa City, both of Iowa

[73] Assignee: University of Iowa Research Foundation, Iowa City, Iowa

[21] Appl. No.: 35,845

[22] Filed: Apr. 8, 1987

[51] Int. Cl.$^4$ ............................................. G01N 27/30
[52] U.S. Cl. .................... 204/1 T; 204/418; 556/95
[58] Field of Search .............. 204/418, 417, 1 T; 436/103, 105; 556/95

[56] References Cited

U.S. PATENT DOCUMENTS 3,445,365  5/1969  Ross ............................. 204/417

FOREIGN PATENT DOCUMENTS 842546  6/1981  U.S.S.R. ......................... 204/418

OTHER PUBLICATIONS

Zarinski, V. A. et al., Electrochemical Properties of Liquid Membranes on Dialkyltin (IV) Compounds in Phosphorus(V) Solutions, UDC 543.257.5:546.18, V. I. Vernadskii Institute of Geochemistry and Analytical Chemistry, Acad. of Sci. of the USSR, Moscow, Translated from Zhurnal Analiticheskoi Khimii, vol. 35, No. 11. pp. 2137-2142-Nov., 1980.

Zarinski, V. A. et al., Dialkyltin(IV) Compounds as Active Components of the Liquid Membranes of Ion-Selective Electrodes in Arsenic(V) Solutions, UDC 543.257.1:546.19, V. I. Vernadskii Institute of Geochemistry and Analytical Chemistry, Academy of Sciences of the USSR, Moscow, Translated from Zhurnal Analiticheskoi Khimii, vol. 35, No. 11, pp. 2143-2148, Nov., 1980.

Primary Examiner—G. L. Kaplan
Attorney, Agent, or Firm—Henderson & Sturm

[57] ABSTRACT

A novel ion-selective membrane electrode for the determination of phosphate anions. This device possesses an excellent selectivity for phosphate over many common anions such as sulfate, chloride, bromide, iodide, nitrate, and acetate. The unique feature of this electrode is the use of a di-substituted aryl tin compound as the membrane active material. The incorporation of either dibenzyltin dichloride or bis-p-methylbenzyltin dichloride in a plasticized poly(vinyl) chloride membrane results in a selective membrane electrode for phosphate.

2 Claims, 3 Drawing Sheets

PHOSPHATE SELECTIVE MEMBRANE ELECTRODE AND METHOD OF DETERMINING PHOSPHATE

TECHNICAL FIELD

This invention relates to ion-selective membrane electrodes, and more particularly to an electrode having selectivity for phosphate anions.

BACKGROUND ART

Many methods for the determination of phosphate ion have been demonstrated in the areas of gravimetric, titrimetric, and spectrophotometric analysis. Included in the methods available, as a minor technique, is the determination of phosphate with ion-selective electrodes. The obvious reason for the lack of use of electrodes is the poor selectivity of the phosphate electrodes constructed to date.

Presently known potentiometric membrane electrodes for anions display a selectivity pattern known as the Hoffmeister series. The well known Hoffmeister series ranks anions in order of decreasing hydrophobicity. It is commonly thought that electrode selectivity for anions is governed by the ability of the anion to enter the hydrophobic polymer membrane. Of course, this ability is greater for more hydrophobic anions and as a result a Hoffmeister series-type selectivity pattern is attained. The Hoffmeister series for several common anions is as follows:

perchlorate > thiocyanate > iodide > nitrate > bromide > chloride > bicarbonate > phosphate > carbonate > sulfate Hence, selectivity for conventional anion electrodes is quite good for perchlorate and thiocyanate, but it is extremely poor for phosphate and sulfate.

The first membrane electrode with a selectivity pattern different than the Hoffmeister series was that for carbonate (Rechnitz, Science 184 (1974) 1074; Wise, U.S. Pat. No. 3,723,281, 1973). This electrode utilizes trifluoroacetyl-p-butylbenzene as the membrane active component. A recent study indicates that this material acts as a neutral carrier for carbonate by complexing with carbonate at the electron-deficient carbon of the carbonyl group to form a hydrophobic carbonate dianion species (Meyerhoff, Anal. Chem. 59 (1987) 144). This electrode is employed in various commercial instruments for carbonate determinations because of its excellent selectivity.

A group of Russian Workers have reported, and patented, the use of dialkyltin dinitrates as a selective reagent for phosphate electrodes. (U.S.S.R. Pat. No. SU 721731, Mar. 15, 1980; Zarinski, V.A. et al., Electrochemcial Properties of Liquid Membranes Based On Dialkyltin(IV) Compounds In Phosphorus(V) Solutions, UDC 543.257.5:546.18, V.I. Vernadskii Institute of Geochemistry and Analytical Chemistry, Academy of Sciences of the USSR, Moscow. Translated from Zhurnal Analiticheskoi Khimii, Vol. 35, No. 11, pp. 2137-2142, November, 1980; and Zarinski, V.A. et al., Dialkyltin(IV) Compounds as Active Components of the Liquid Membranes of Ion-Selective Electrodes in Arsenic(V) Solutions, UDC 543.257.1:546.19, V.I. Vernadskii Institute of Geochemistry and Analytical Chemistry, Academy of Sciences of the USSR, Moscow. Translated from Zhurnal Analiticheskoi Khimii, Vol. 35, No. 11, pp. 2143-2148, November, 1980). Their electrode system responds only to high levels of phosphate (10-100 mM) and its selectivity properties have not been thoroughly explored. In addition, their system apparently must use a liquid membrane electrode configuration, and the membrane active material is dioctyltin dinitrate. Other work based on substituted tin compounds has been reported, but no electrodes with a selective response to phosphate have been reported.

There is a tremendous need for a phosphate selective electrode in nearly all areas of science and technology. This need is based on the overall importance of phosphate and the current lack of suitable analytical procedures for phosphate determination. Phosphate levels are important in a wide variety of situations based on the importance of phosphate in biochemical and physiological processes, the presence of phosphates in fertilizers and minerals, and the magnitude of phosphates in industrial water processing. Despite the overall significance of phosphate, the development of a selective electrode system for phosphate has not been successful. In a recent review of phosphate electrode attempts, Midgley (ISE Reviews, 8 (1986) 3) reports "None of the experimental designs has reached commercial production and the work so far does little to suggest that good selectivity can be achieved." This statement points out that none of the many attempts have successfully resulted in a selective phosphate system and that there is little promise that these strategies will be successful in the future.

Those concerned with these and other problems recognize the need for an improved phosphate selective membrane electrode.

DISCLOSURE OF THE INVENTION

The present invention provides a novel ion-selective membrane electrode for the determination of phosphate anions. This device possesses an excellent selectivity for phosphate over many common anions such as sulfate, chloride, bromide, iodide, nitrate, and acetate. The unique feature of this electrode is the use of a di-substituted aryl tin compound as the membrane active material. The incorporation of either dibenzyltin dichloride or bis-p-methylbenzyltin dichloride in a plasticized poly(vinyl) chloride membrane results in a selective membrane electrode for phosphate.

The novel feature of the present electrode system is the use of dibenzyltin dichloride, and related derivatives, as the membrane active component. The present system responds to low phosphate levels (0.01-10 mM) and the selectivity has been firmly established under rigorously controlled conditions. Further, the present system uses the more convenient and practical polymer-based membrane configuration where the membrane active material is dibenzyltin dichloride. The difference in chemical properties of the present system results in superior response characteristics when compared to the Zarinskii system.

An object of the present invention is the provision of an improved phosphate selective membrane electrode.

Another object is to provide a phosphate selective electrode that responds to low phosphate levels.

A further object of the invention is the provision of a phosphate selective electrode that employs a convenient and practical polymer-based membrane configuration.

Still another object is to provide a phosphate selective electrode that uses dibenzyl tin dichloride, and related derivatives, as the membrane active component.

A still further object of the present invention is the provision of a phosphate selective electrode that has superior response characteristics.

Yet another object is to provide a phosphate selective electrode useful for simultaneously determining the phosphate ion as well as the interferent ions.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 1:
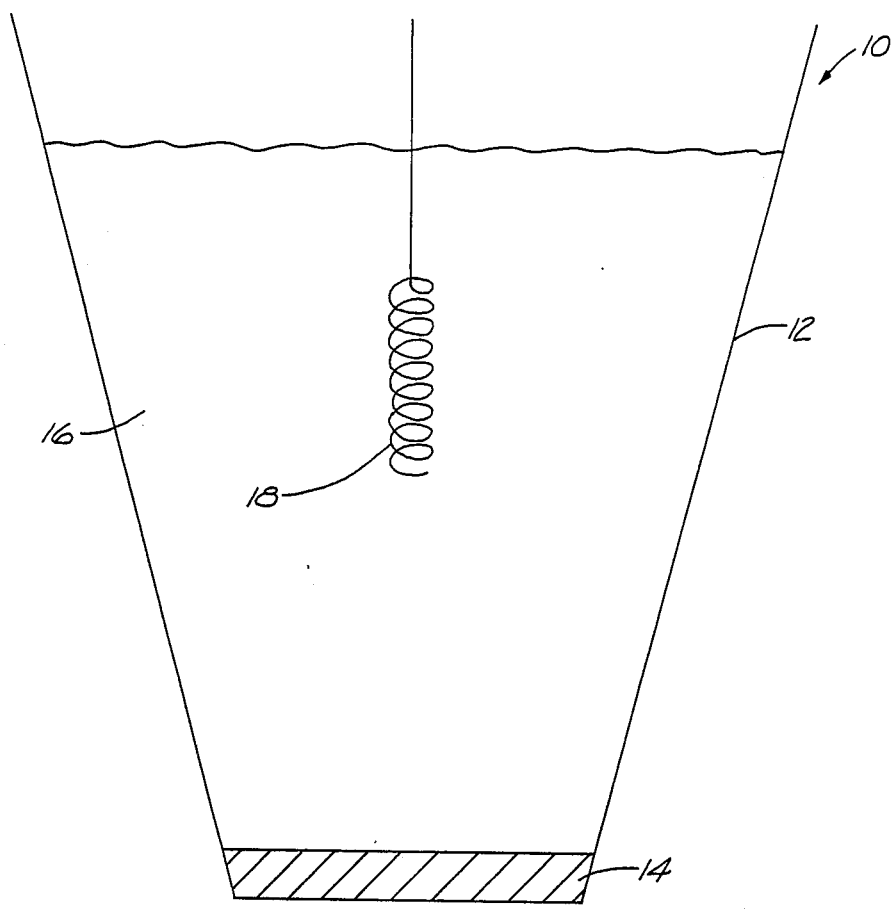
FIG. 1 is a schematic representation of the disclosed phosphate selective membrane electrode.

Referring now to the drawings, wherein like reference numerals designate identical or corresponding parts throughout the several views, FIG. 1 shows the phosphate selective membrane electrode generally designated by the reference numeral 10. The electrode (10) includes a body section (12) having a lower opening sealed by a phosphate selective membrane (14). The body section (12) contains an internal reference solution (16) and an internal reference electrode (18). The phosphate selective membrane (14) owes its sensitivity to a di-substituted aryl tin compound used as a membrane active component. Studies show that the incorporation of either dibenzyltin dichloride or bis-p-methyltin dichloride in a plasticized poly(vinyl) chloride membrane forms a membrane (14) possessing an excellent selectivity for phosphate over many common anions.

Figure 2:
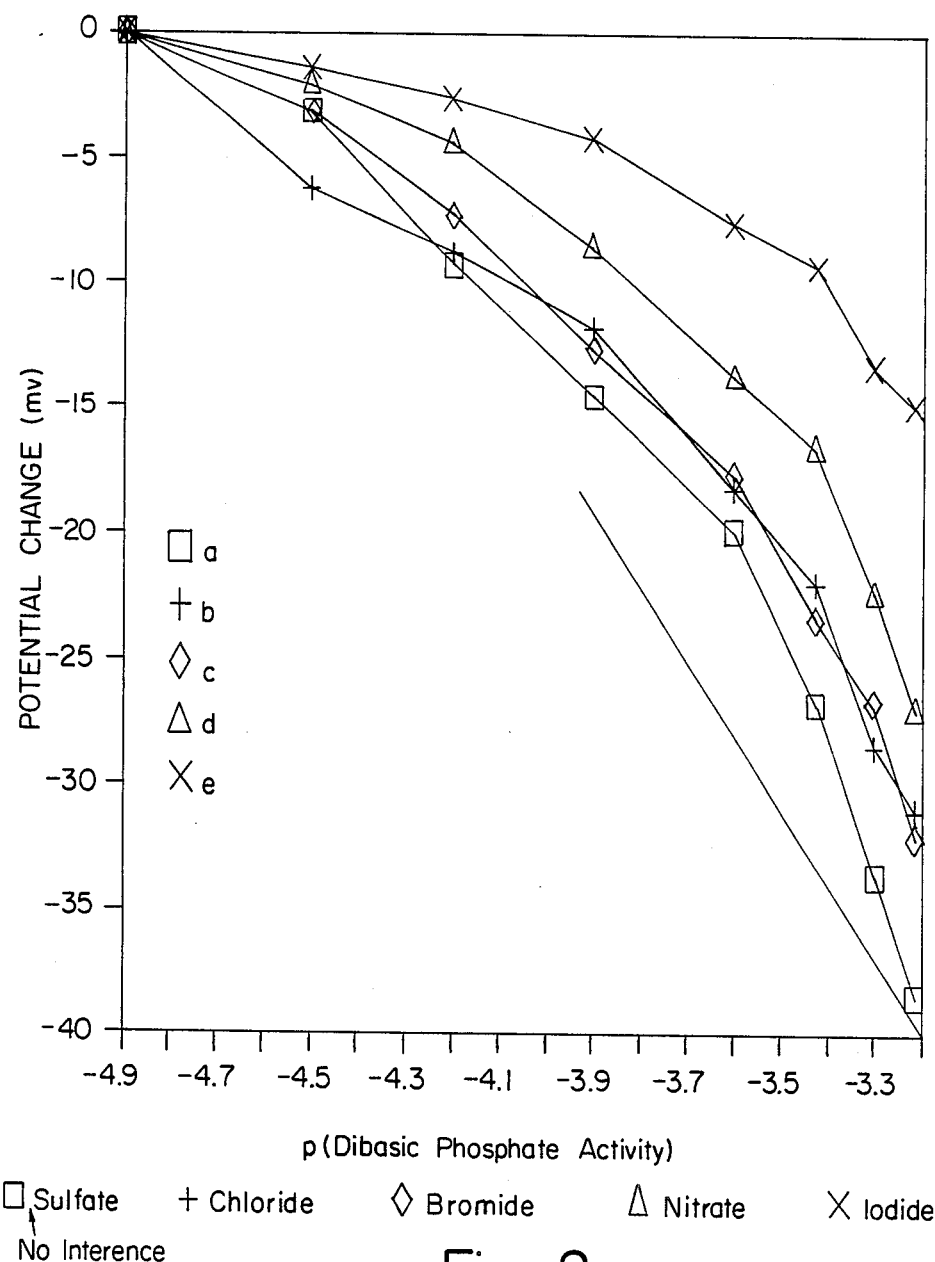
FIG. 2 is a graph showing the response performance of the phosphate electrode (with dibenzyltin dichloride) in a 0.01 M Tris-sulfate buffer, pH 7.0.

FIG. 2 shows the response performance of the electrode (10) in a 0.01 M Tris-sulfate buffer, pH 7, wherein the membrane (14) includes dibenzyltin dichloride as a membrane active component. The response performed is shown with (a), a buffer only; (b), 1 mM chloride; (c), 1 mM bromide; (d), 1 mM nitrate; and (e), 1 mM iodide.

Figure 3:
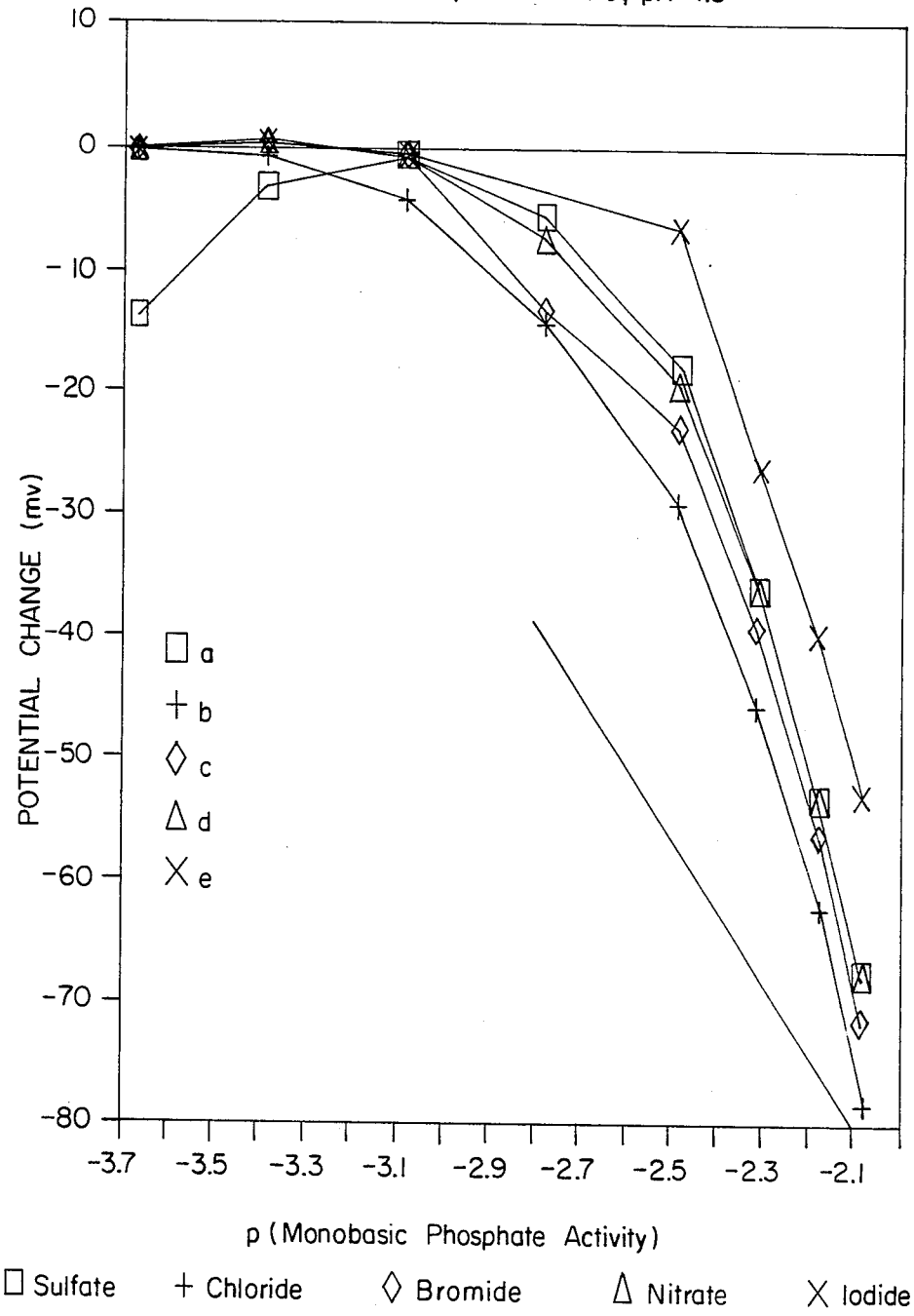
FIG. 3 is a graph showing the response performance of the phosphate electrode (with dibenzyltin dichloride) in a 0.01 M acetate/sulfate buffer pH 4.3.

FIG. 3 shows the response performance of the electrode (10) in a 0.01 M acetate/sulfate buffer, pH 4.3, wherein the membrane active component is again dibenzyltin dichloride. The graph shows the response performance with (a), buffer alone; (b), 1 mM chloride; (c), 1 mM bromide; (d), 1 mM nitrate; and (e), 1 mM iodide.

For binary samples, samples containing only phosphate and a single interferent, electrodes (10) may successfully be utilized if techniques for multicomponent analysis are adopted. These techniques, as applied here, are intended to determine the ion of interest as well as the interferent simultaneously.

Complete knowledge is lacking concerning the fundamental response characteristics and the response mechanism of the electrode (10). However, based on current selectivity information, the electrode (10) of the present invention is capable of working in relatively simple aqueous solutions with common anions, such as chloride, nitrate, bromide, iodide, sulfate, and acetate. Applications for phosphate determinations in industrial process control systems and in environmental monitoring are certainly possible. Also, it can be speculated that this electrode will be useful in clinical, biomedical, and dental research; however, the extent of interferences is much higher and complicated in these latter areas and more selectivity characterization is required.

Thus, it can be seen that at least all of the stated objectives has been achieved.

Obviously, many modifications and variations of the present invention are possible in light of the above teachings. It is therefore to be understood that, within the scope of the appended claims, the invention may be practised otherwise than as specifically described.

We claim:

1. A phosphate ion selective membrane electrode comprising:
   a body member having an opening therein;
   a membrane sealably attached to said body member over said opening, said membrane including a di-substituted aryl tin compound selected from a group consisting of dibenzyltin dichloride and derivatives thereof;
   a reference solution contained within said body member; and
   a reference electrode disposed withn said body member in contact with said reference solution.

2. A method of determining the phosphate anion in a sample including the step of:
   contacting said sample with the electrode of claim 1.

* * * * *